United States Patent
Doron et al.

(12) 
(10) Patent No.: US 6,486,588 B2
(45) Date of Patent: Nov. 26, 2002

(54) ACOUSTIC BIOSENSOR FOR MONITORING PHYSIOLOGICAL CONDITIONS IN A BODY IMPLANTATION SITE

(75) Inventors: Eyal Doron, Kiryat Yam (IL); Avi Penner, Tel Aviv (IL)

(73) Assignee: Remon Medical Technologies LTD (IL)

(*) Notice: Subject to any disclaimer, the term of this patent is extended or adjusted under 35 U.S.C. 154(b) by 0 days.

(21) Appl. No.: 09/872,129

(22) Filed: Jun. 1, 2001

(65) Prior Publication Data
US 2001/0026111 A1 Oct. 4, 2001

Related U.S. Application Data

(63) Continuation of application No. 09/523,413, filed on Mar. 10, 2000, which is a continuation-in-part of application No. 09/000,553, filed on Dec. 30, 1997, now Pat. No. 6,140,740.

(51) Int. Cl.⁷ .............................................. H01L 41/08
(52) U.S. Cl. ......................... 310/322; 310/321; 600/300
(58) Field of Search ................. 310/334, 324, 310/322, 317, 319, 321; 600/300; 128/899

(56) References Cited

U.S. PATENT DOCUMENTS

| | | | | |
|---|---|---|---|---|
| 3,568,661 A | * | 3/1971 | Franklin ...................... | 128/2.05 |
| 3,757,770 A | * | 9/1973 | Brayshaw et al. .......... | 128/2 R |
| 4,127,110 A | * | 11/1978 | Bullara ........................ | 128/2 P |
| 4,227,407 A | * | 10/1980 | Drost ......................... | 73/194 A |
| 4,519,401 A | * | 5/1985 | Ko et al. ...................... | 118/748 |
| 4,541,431 A | * | 9/1985 | Ibrahim et al. .............. | 128/419 |
| 4,593,703 A | * | 6/1986 | Cosman ...................... | 128/748 |
| 4,600,855 A | * | 7/1986 | Strachan ..................... | 310/338 |
| 4,653,508 A | * | 3/1987 | Cosman ...................... | 128/748 |
| 4,660,568 A | * | 4/1987 | Cosman ...................... | 128/748 |
| 4,676,255 A | * | 6/1987 | Cosman ...................... | 128/748 |

(List continued on next page.)

FOREIGN PATENT DOCUMENTS

| | | |
|---|---|---|
| EP | 0 897 690 A1 | 2/1999 |
| WO | WO 8303345 A1 | 10/1983 |
| WO | WO 97/01986 A1 | 1/1997 |
| WO | WO 97/33513 A1 | 9/1997 |
| WO | WO 97/47236 A1 | 12/1997 |
| WO | WO 98/26716 A1 | 6/1998 |
| WO | WO 98/29030 A1 | 7/1998 |
| WO | WO 99/26530 A1 | 6/1999 |
| WO | WO 99/59460 A3 | 11/1999 |
| WO | WO 99/59460 A2 | 11/1999 |
| WO | WO 00/16686 A2 | 3/2000 |

OTHER PUBLICATIONS

E. R. Cosman et al. (Massachussetts, Apr. 1979) "A Telemetric Pressure Sensor for Ventricular Shunt Systems" *Surgical Neurology* vol. 11, No. 4, pp. 287–294.

(List continued on next page.)

*Primary Examiner*—Brian Sircus
*Assistant Examiner*—Michael C. Zarroli
(74) *Attorney, Agent, or Firm*—Bingham McCutchen LLP

(57) ABSTRACT

An acoustic biosensor is provided for deployment at an implantation site within a body, such as an abdominal aortic aneurysm. The biosensor includes a sensor element for measuring a physiological condition at the implantation site, and for generating an information signal representative of the physiological condition. The biosensor further includes a piezoelectric transducer element for converting an externally originated acoustic interrogation signal into energy for operating the sensor, and for modulating the interrogation signal, e.g., by employing a switching element to alternate the mechanical impedance of the transducer element, to transmit the information signal outside of the body.

11 Claims, 8 Drawing Sheets

U.S. PATENT DOCUMENTS

| | | | | |
|---|---|---|---|---|
| 4,781,715 A | * | 11/1988 | Wurzel | 623/3 |
| 4,846,191 A | * | 7/1989 | Brockway et al. | 128/748 |
| 5,024,224 A | * | 6/1991 | Engebretson | 128/420.6 |
| 5,178,153 A | * | 1/1993 | Einzig | 128/692 |
| 5,289,821 A | * | 3/1994 | Swartz | 128/661.09 |
| 5,314,457 A | * | 5/1994 | Jeutter et al. | 607/116 |
| 5,339,051 A | * | 8/1994 | Koehler et al. | 331/65 |
| 5,411,551 A | * | 5/1995 | Winston et al. | 623/1 |
| 5,423,334 A | * | 6/1995 | Jordan | 128/899 |
| 5,476,488 A | * | 12/1995 | Morgan et al. | 607/30 |
| 5,562,714 A | * | 10/1996 | Grevious | 607/32 |
| 5,571,152 A | | 11/1996 | Chen et al. | 607/92 |
| 5,656,428 A | * | 8/1997 | McAllister et al. | 435/6 |
| 5,704,352 A | | 1/1998 | Tremblay et al. | 128/630 |
| 5,733,313 A | | 3/1998 | Barreras, Sr. et al. | 607/33 |
| 5,735,887 A | | 4/1998 | Barreras, Sr. et al. | 607/60 |
| 5,741,316 A | | 4/1998 | Chen et al. | 607/61 |
| 5,807,258 A | | 9/1998 | Cimochowski et al. | 600/454 |
| 5,810,009 A | * | 9/1998 | Mine et al. | 600/459 |
| 5,832,924 A | | 11/1998 | Archibald et al. | 128/672 |
| 5,833,603 A | | 11/1998 | Kovacs et al. | 600/317 |
| 5,843,135 A | | 12/1998 | Weijand et al. | 607/17 |
| 5,856,722 A | * | 1/1999 | Haronian et al. | 310/321 |
| 5,873,835 A | | 2/1999 | Hastings et al. | 600/488 |
| 5,957,950 A | | 9/1999 | Mockros et al. | 606/194 |
| 5,967,986 A | | 10/1999 | Cimochowski et al. | 600/454 |
| 6,053,873 A | | 4/2000 | Govari et al. | 600/505 |
| 6,277,078 B1 | * | 8/2001 | Porat et al. | 600/486 |
| 6,368,275 B1 | * | 4/2002 | Sliwa et al. | 600/437 |
| 6,397,661 B1 | * | 6/2002 | Grimes et al. | 73/24.06 |

OTHER PUBLICATIONS

Z. Tang et al. (May 1995) "Data Transmission from an Implantable Biotelemeter by Load–Shift Keying Using Circuit Configuration Modulator" *IEEE Transactions on Biomedical Engineering*. vol. 42, No. 5, pp. 524–528.

Dipl.–Ing. Torsten Eggers et al. (Germany) "Implantable Telemetric Endosytem (ITES)" *IMSAS Institut Fur Mikrosensoren–Aktuatoren Und–Systeme*. 2 pp.

T. Chuter et al. (Sweden, Jan. 1997) "Aneurysm Pressure Following Endovascular Exclusion" *Eur. J. Vasc. Endovasc. Surg*. vol. 13, pp. 85–87.

Prof. Dr. Johannes Zacheja et al. (Germany, Sep. 1996) "An Implantable Microsystem For Biomedical Applications" *Micro System Technologies 96*, pp. 717–722.

C. Hierold et al. (Germany, 1998) "Implantable Low Power Integrated Pressure Sensor System For Minimal Invasive Telemetric Patient Monitoring" *IEEE*, pp. 568–573.

Dr. Hartmut Runge (Germany, May 1998) "Implanted blood pressure sensor reduces risk of infection for patients hospitalized for long–term observation" *Siemens Press Release* pp. 1–2.

Karl E. Richard et al. (Germany, Jan. 1999) "First clinical results with a telemetric shunt–integrated ICP–sensor" *Neurological Research* vol. 21, pp. 117–120.

T.A. Cochran et al. (1990) "Aortic Aneurysm Abdominal", *Current Therapy in Adult Medicine*, Fourth Edition.

G.W.H. Schurink et al. (1998) "Late Endoleak After Endovascular Therapy for Abdominal Aortic Aneurysm" Eur. J. Vasc. Endovasc. Surg. vol. 17, pp. 448–450.

GH White et al. (1997) "Endoleak Following Endoluminal Repair of AAA: Management Options and Patient Outcomes", J. *Endovasc Surg*, pp. 1–45.

S.K. Gupta et al. (1999) "Use of a Piezoelectric Film Sensor for Monitoring Vascular Grafts", *The American Journal of Surgery*, vol. 160, pp. 182–186.

* cited by examiner

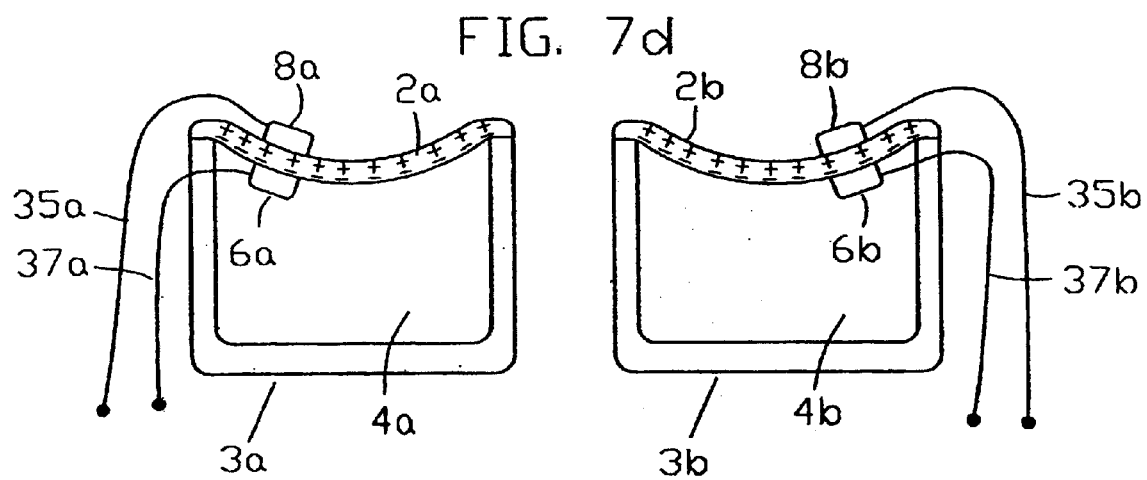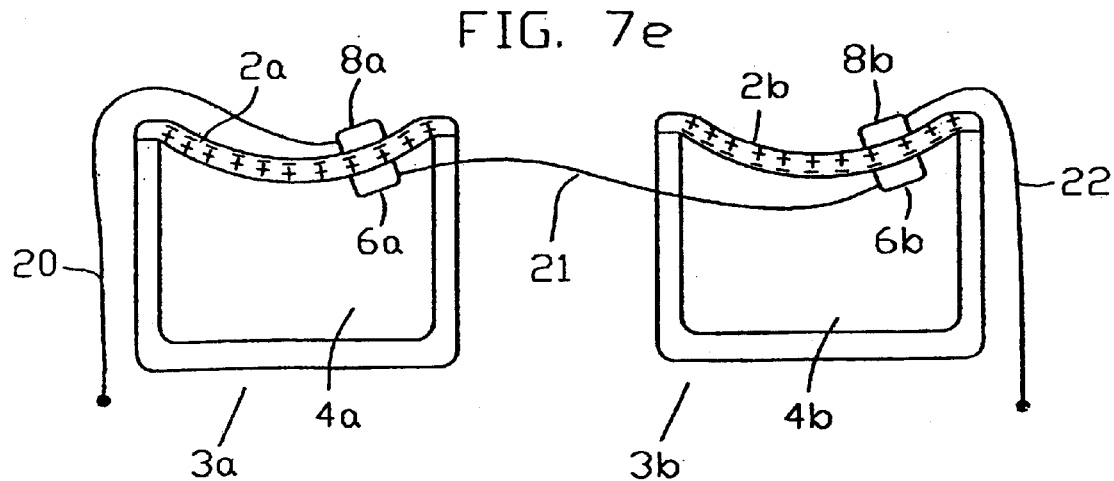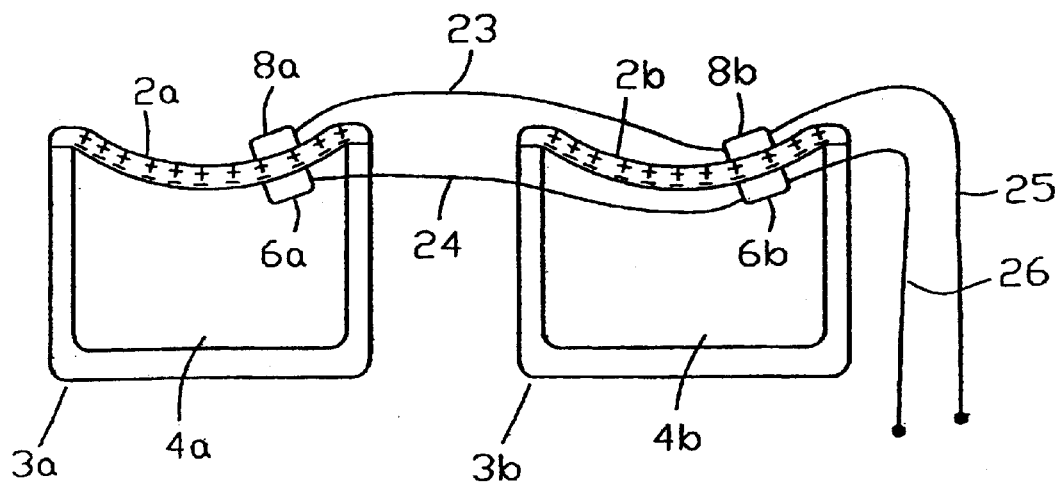

ACOUSTIC BIOSENSOR FOR MONITORING PHYSIOLOGICAL CONDITIONS IN A BODY IMPLANTATION SITE

RELATED APPLICATION DATA

This application is a continuation application of Ser. No. 09/523,413 filed on Mar. 10, 2000, which is a Continuation-In-Part of pending application Ser. No. 09/000,553, filed on Dec. 30, 1997 now U.S. Pat. No. 6,140,740.

FIELD OF INVENTION

The present invention pertains generally to the field of implantable biosensors and, in particular, to methods and apparatus for monitoring physiological conditions in a patient using a biosensor at an implantation site in the body, such as, e.g., an aneurysmal sac, equipped with an acoustic telemetry and energy conversion mechanism.

BACKGROUND

An aneurysm is an abnormal ballooning of the wall of an artery that results from the weakening of the artery due to injury, infection, or other conditions, such as a congenital defect in the arterial connective tissue. Common forms of such an aneurysm include an abdominal aortic aneurysm, an iliac aneurysm, a bifurcated aneurysm of the abdominal aorta and the iliac, and a thoracic aortic aneurysm.

The aorta, which is the main arterial link in the circulatory system, begins at the left ventricle of the heart, forms an arch above the heart, and passes behind the heart, continuing downward through the thorax and the abdomen. Along this path, the abdominal aorta branches into two vessels, called the renal arteries, that supply blood to the kidneys. Below the level of the renal arteries, the abdominal aorta extends approximately to the level of the fourth lumbar vertebra, where it branches into the iliac arteries. The iliac arteries, in turn, supply blood to the lower extremities and the perineal region.

Abdominal aortic aneurysms can occur in the portion of the abdominal aorta between the renal and the iliac arteries. This condition, which is most often seen in elderly men, often leads to serious complications, including rupture of the aneurysmal sac. A ruptured aneurysm occurs in approximately 3.6 out of 10,000 people and is considered a medical emergency, since the resultant rapid hemorrhaging is frequently fatal.

There are generally two methods for treating abdominal aortic aneurysms: (1) surgical repair of the aneurysm, and (2) endoluminal stent graft implantation. Surgical repair of the aneurysm involves the implantation of a tubular prosthetic vascular graft, traditionally made of fluoropolymers, such as polytetrafluoroethylene (PTFE) or polyester (Dacron), into the aorta. These prosthetic vascular grafts traditionally have been implanted by open surgical techniques, whereby a diseased or damaged segment of the blood vessel is surgically cut along its longitudinal axis and the tubular bioprosthetic graft is then inserted coaxial to the original artery and anastomosed within the host blood vessel as an internal replacement for the diseased segment. Then the longitudinal cut in the artery is sutured. Alternatively, prosthetic vascular grafts have been used as bypass grafts wherein opposite ends of the graft are sutured to the host blood vessel in order to form a conduit around the diseased, injured, or occluded segment of the host vessel.

These surgical approaches suffer from similar disadvantages, namely, the extensive recovery period associated with major abdominal surgery, the difficulties in suturing the graft to the aorta, the unsuitability of surgery for many at-risk patients, and the high mortality and morbidity rates associated with surgical intervention of this magnitude.

The second approach to treating an abdominal aortic aneurysm, endolumenal stent graft implantation, overcomes many of these disadvantages. An endoluminal stent graft normally consists of a vascular graft that is supported by a metallic stent skeleton over a portion of the length of the graft. By introducing and deploying the stent graft through the lumen of the blood vessel, a surgeon may then repair the damaged aortic segment using only percutaneous or minimal incisions in the patient. This technique initially involves translumenal delivery of the graft in a compacted low profile configuration by way of a catheter or some other transluminally advancable delivery apparatus. The stent is then radially expanded, thereby anchoring the graft to the surrounding blood vessel wall and sealing off the aneurysm from the rest of the circulatory system. As a result, the pressure within the isolated aneurysmal sac and the endotension of the artery are both reduced.

It is generally agreed that such endoluminal stent grafts work best in patients with small- to medium-sized abdominal aortic aneurysms, or in patients with large abdominal aortic aneurysms who are characterized as high risk candidates for open surgical abdominal aortic aneurysm repair. In addition to treating vascular aneurysms, an endovascular stent graft may also be used to treat occlusive vascular disease.

In some instances, the stented graft is constructed in such a manner that the tubular graft material forms a complete barrier between the stent and the blood, which is flowing through the blood vessel. In this way, the tubular graft material serves as a smooth, biologically compatible inner lining for the stent. Graft material known in the prior art includes woven or knitted fabrics, such as polyester fiber, or a porous form of PTFE known as ePTFE.

The major complication involved in the endolumenal stent graft implantation is the formation of an endoleak. An endoleak is defined as blood leakage into the aneurysmal sac causing the sac to fill with blood and increasing the endotension. Endotension is defined by the internal pressure within the aneurysm, the aneurysm diameter and wall thickness. In particular, endotension is a physical parameter that indicates the chances of aneurysm rupture. The implantation of a stent graft prevents blood from filling the aneurysmal sac, resulting in a depressurization of the sac with minimal influence on the aneurysm wall thickness. The diameter of the aneurysm might change with pressure reduction, but the direct parameter that vanes is the pressure.

Endoleaks can be divided into four categories: Type I, which results from leakage due to insufficient sealing of the graft against the aortic wall; type II, which results from blood flow to the aneurysmal sac through bypass arteries; type III, which arises from mechanical failure of the graft system; and type IV, which arises from leakage through the graft fabric due to the porosity of the material.

Because of the high risk of aneurysmal rupture, the early detection of endoleaks resulting in endotension is crucial. With early detection, the pressure within the aneurysmal sac may be reduced through endovascular treatment (balloon inflation or additional stent graft implantation for improve sealing) or a surgical intervention. Currently, the standard method for the detection of endoleaks is through contrast-enhanced computerized tomography (CT), which relies on the x-ray imaging of the abdominal region after injection of a contrast media in order to improve the detection of blood and vascular tissue. If an endoleak is present, then the aneurysmal sac will fill with contrast media and the endoleak will then be identified in the resultant CT scan.

Although CT scans are considered a reliable method for detecting endoleaks, they suffer from several disadvantages. First, CT scans require an experienced operator and an expensive apparatus, placing significant financial constraints on its frequency of use. Second, the CT scan procedure exposes the patient to x-ray radiation and cannot be used as frequently as desired. Third, CT scans can only provide an estimate of the pressure within the aneurysm indirectly by detecting leakage into the aneurysmal sac, and are unable to detect small leaks that may cause slow, but potentially dangerous, pressurization within the aneurysm.

In addition to CT scans, ultrasound imaging methods have also been used to detect endoleaks. Ultrasound-based methodologies posses several advantages over CT, including a simpler apparatus and the absence of ionizing radiation. Consequently, such imaging can be performed more often and at a lower cost than CT scans. However, ultrasound-based imaging is operator dependent and less reliable than CT scans.

Endoleaks may also be detected by directly monitoring the internal pressure within an aneurysmal sac. For example, published EPO application EP 0 897 690 A1 ("van Bockel"), which is fully incorporated herein by reference for all that it teaches and discloses, discloses the placement of a pressure sensing device in an aneurysmal sac in conjunction with the placement of an endoprosthesis. The van Bockel device includes a pressure sensor and a transponder capable of wireless transmission of data obtained from the sensor back out of the body. However, the transponder device proposed by Van Bockel employs electric or magnetic fields to transmit the pressure data. Because of the high absorption of electromagnetic energy by human or animal tissue, the intra-body positioning of such a device may be limited to regions close to the skin, which are accessible to electromagnetic signals. In particular, it is unclear how effective such a device would be in detecting endoleaks, since abdominal aortic aneurysms are deeply embedded within the body. Accordingly, biosensors implanted therein that rely on the electromagnetic signaling disclosed by Van Bockel may function unreliably.

Thus, there exists a need for more accurate and reliable methods and apparatus for direct monitoring of the internal pressure within an aneurysmal sac, and for efficient and reliable communication of such data out of the body.

SUMMARY OF THE INVENTION

In accordance with a first aspect of the invention, preferred constructions and embodiments of an acoustic powered telemetric biosensor are provided for deployment at an implantation site within a body, such as an abdominal aortic aneurysm.

In a preferred embodiment, the biosensor comprises a sensor element for measuring a physiological condition at the implantation site, and for generating an information signal representative of the physiological condition. The biosensor further comprises a piezoelectric transducer element for converting an externally originated acoustic interrogation signal into energy for operating the sensor, and for modulating the interrogation signal (e.g., by employing a switching element to alternate the mechanical impedance of the transducer element) to transmit the information signal outside of the body.

The transducer element is preferably tailored so as to allow the usage of low frequency acoustic interrogation signals for vibrating the piezoelectric layer at its resonant frequency, wherein substantially low frequency signals herein refer to signals having a wavelength that is much larger than dimensions of the transducer. The use of such low frequency signals allows for reliable transmission of the acoustic waves to and from deep body implant sites. Further, the transducer element is preferably shaped so as to maximize its electrical output. Preferred embodiments of the transducer element may be integrally manufactured with any combination of electronic circuits by using photolithographic and microelectronics technologies.

As will be apparent to those skilled in the art, other and further aspects of the present invention will appear hereinafter.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which:

FIGS. 2a–2e are cross sections of the transducer element, taken at the respective sections C, D, E, F and G shown in FIG. 1a;

FIGS. 7a–7f are schematic views of possible configurations of acoustic biosensor transmitters constructed in accordance with the present invention, including parallel and anti-parallel electrical connections for controllably changing the mechanical impedance of the piezoelectric layer;

DETAILED DESCRIPTION OF THE PREFERRED EMBODIMENTS

An acoustic biosensor constructed in accordance with the present invention functions to deliver physiologic data from an implantation site within a human or animal body to an external instrument. Depending on the particular implementation site and needs of the patient, the biosensor may comprise any of a number of sensor types, such as a sensor selected from the group consisting of a pressure sensor, a temperature sensor, a position sensor, a tactility sensor, an electrical impedance sensor, a pH sensor, a blood sugar sensor, a blood oxygen sensor, a motion sensor, a flow sensor, a velocity sensor, an acceleration sensor, a force sensor, a strain sensor, an acoustics sensor, a moisture sensor, an osmolarity sensor, a light sensor, a turbidity sensor, a radiation sensor, an electrical energy sensor, an electromagnetic field sensor, a chemical sensor, an ionic sensor, and an enzyme sensor. Further, the biosensor may comprise multiple sensors of a single type, or a mix of various types and quantities of sensors, depending on the implantation site and application.

As set forth herein, a preferred biosensor is constructed in accordance with the teachings of U.S. patent application Ser. No. 09/303,644, which is fully incorporated by reference for all that it teaches and discloses. As taught therein, acoustic energy received from an externally originated interrogation signal is converted by a specially constructed piezoelectric transducer element into a current supply for powering one or more sensors embedded in the biosensor for measuring various biological parameters at the implantation site. The biosensor employs a switching element to alternate the mechanical impedance of the transducer element to modulate the interrogation signal to thereby transmit the measured information, i.e., representative of the physiological condition at the implantation site, external to the body. A suitable transceiver outside of the body may be utilized to detect and interpret this modulated signal, as well as to emit the originating interrogation signal.

Figure 10:
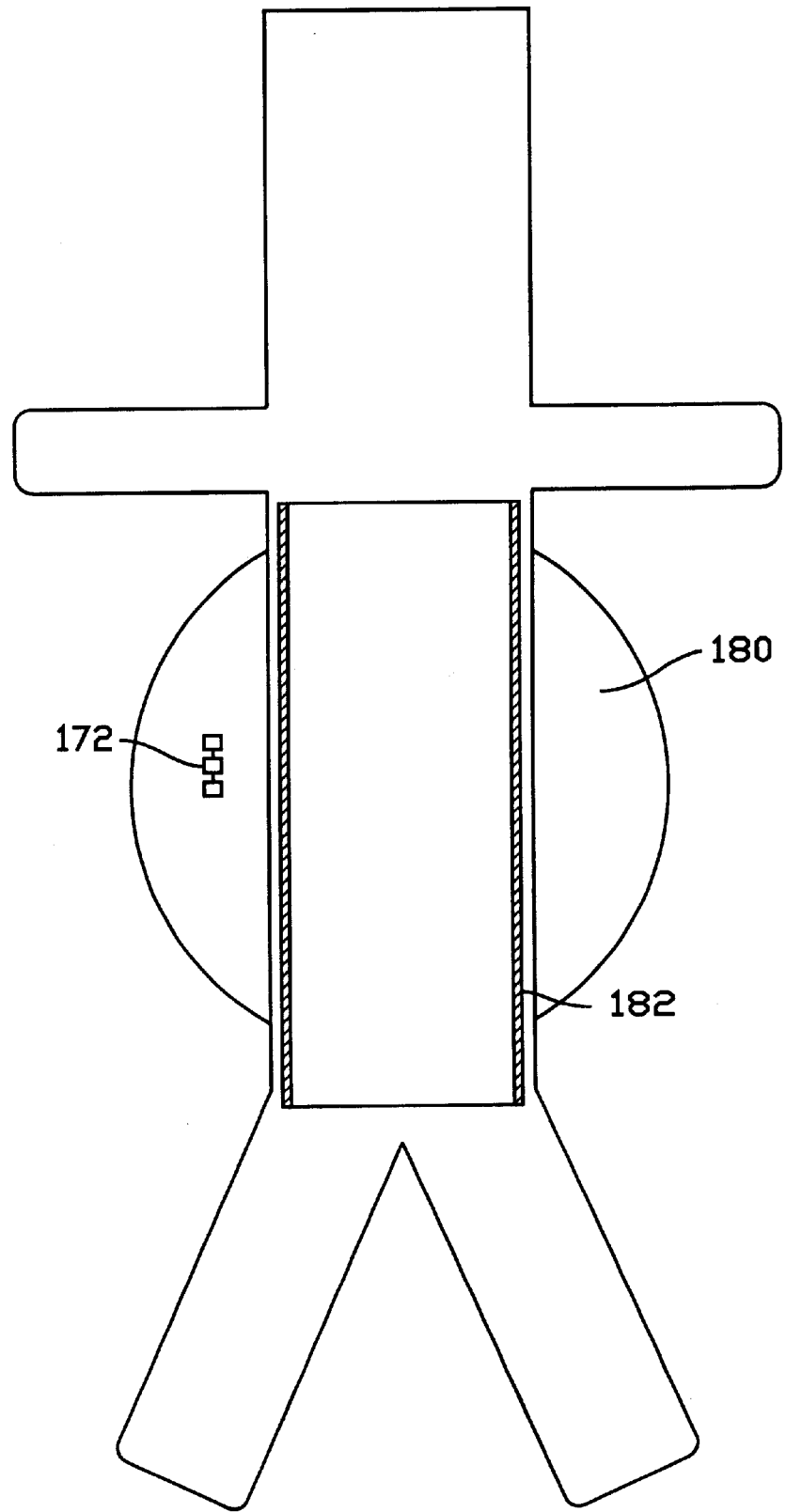
FIG. 10 depicts a simplified abdominal aortic aneurysm in which an acoustic powered telemetric biosensor constructed in accordance with the present invention has been deployed in conjunction with a stent graft.

By way of illustration, with reference to FIG. 10, an acoustic powered telemetric biosensor 172 is shown implanted in an abdominal or thoracic aortic aneurysmal sac 180 in conjunction with a stent graft 182. In particular, by transmitting biological measurements in response to an externally generated interrogation signal (as described below), the biosensor 172 provides for more precise monitoring of the aneurysmal sac 180 following the implantation of the stent graft 182.

As will be appreciated by those skilled in the art, the biosensor 172 may occupy several possible positions relative to the stent graft 182. For example, the biosensor 172 may be freely disposed within the aneurysmal sac 180, as shown in FIG. 10. Alternatively, the biosensor 172 may be directly attached to the side of the stent graft 182 (not shown), or may be indirectly coupled to the stent graft 182 though a tether (not shown). Any changes in the pressure within the aneurysmal sac 180, for example, may indicate the formation of a potentially dangerous endoleak. Because the biosensor 172 allows for non-invasive pressure measurements, aneurysmal pressure may be evaluated more conveniently and at more frequent intervals, and endoleaks may be more easily detected.

Translumenal delivery of the biosensor 172, either separate from or in conjunction with the stent graft 182, is suitable for positioning the biosensor 172 in the aneuysmal sac 180. Preferred methods and apparatus for delivering a biosensor to a desired implantation site within a human or animal body are provided in U.S. patent application Ser. No. 09/552,370, entitled "Systems and Methods for Deploying a Biosensor in Conjunction with a Prosthesis," Ser. No. 09/522,724, entitled "Systems and Methods for Deploying a Biosensor with a Stent Graft," and Ser. No. 09/523,414, entitled "Methods and Apparatus for Deploying An Implantable Biosensor," each of which was filed on Mar. 10, 2000, and each of which is fully incorporated herein by reference for all that it teaches and discloses. Alternately, the biosensor 172 may also be placed in the aneurysmal sac 180 by a conventional surgical technique. Notably, multiple biosensor 172 may be placed in a given site, if desirable.

FIGS. 1a, 1b and 2a–2e illustrate a first preferred embodiment of a transducer element for use in an implantable acoustic biosensor (e.g., such as biosensor 172 in FIG. 10).

As shown in the figures, the transducer element 1 includes at least one cell member 3 forming a cavity 4 etched into a substrate and covered by a substantially flexible piezoelectric layer 2. Attached to piezoelectric layer 2 are an upper electrode 8 and a lower electrode 6, the electrodes for connection to an electronic circuit. The substrate is preferably made of an electrical conducting layer 11 disposed on an electrically insulating layer 12, such that the cavity 4 is etched substantially through the thickness of electrically conducting layer 11.

Electrically conducting layer 11 is preferably made of copper and insulating layer 12 is preferably made of a polymer such as polyimide. Conventional copper-plated polymer laminate such as Kapton™ sheets may be used for the production of transducer element 1. Commercially available laminates such as Novaclad™ may be used. Alternatively, the substrate may include a silicon layer, or any other suitable material. Alternatively, layer 11 is made of a non-conductive material such as Pyralin™.

The cavity 4 may be etched into the substrate by using conventional printed-circuit photolithography methods. Alternatively, the cavity 4 may be etched into the substrate by using VLSI/micro-machining technology or any other suitable technology. Piezoelectric layer 2 may be made of PVDF or a copolymer thereof. Alternatively, piezoelectric layer 2 is made of a substantially flexible piezoceramic. Preferably, piezoelectric layer 2 is a poled PVDF sheet having a thickness of about 9–28 $\mu$m. Preferably, the thickness and radius of flexible layer 2, as well as the pressure within cavity 4, are specifically selected so as to provide a predetermined resonant frequency. When using the embodiment of FIGS. 1a and 1b, the radius of layer 2 is defined by the radius of cavity 4.

By using a substantially flexible piezoelectric layer 2, the present invention allows to provide a miniature transducer element whose resonant frequency is such that the acoustic wavelength is much larger than the extent of the transducer. This enables the transducer to be omnidirectional even at resonance, and further allows the use of relatively low frequency acoustic signals which do not suffer from significant attenuation in the surrounding medium.

Prior art designs of miniature transducers, however, rely on rigid piezoceramic usually operating in thickness mode. In such cases the resonant frequency relates to the size of the element and speed of sound in the piezoceramic, and is higher by several orders of magnitude. Notably, in a preferred embodiment, the transducer of the present invention is omnidirectional, i.e., insensitive to the direction of the impinging acoustic rays, thereby substantially simplifying the transducer's operation relative to other resonant devices. Such a transducer element is thus suitable for application in confined or hidden locations, where the orientation of the transducer element cannot be ascertained in advance.

In one preferred embodiment, the cavity 4 features a circular or hexagonal shape with radius of about 200 $\mu$m. Electrically conducting layer 11 preferably has a thickness of about 15 μm. Cell member 3 is preferably etched completely through the thickness of electrically conducting layer 11. Electrically insulating layer 12 preferably features a thickness of about 50 μm. The precise dimensions of the various elements of a transducer element according to the present invention may be specifically tailored according to the requirements of the specific application.

Th cavity 4 is preferably filled with a gas such as air, wherein the pressure of gas within cavity 4 may be specifically selected relative to the pressure external to the device (i.e., at the implantation site within a body), so as to adjust the sensitivity and ruggedness of the transducer, as well as the resonant frequency of layer 2.

Figure 2A:
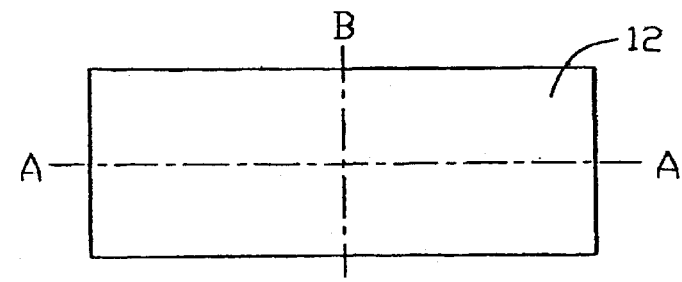
Figure 2B:
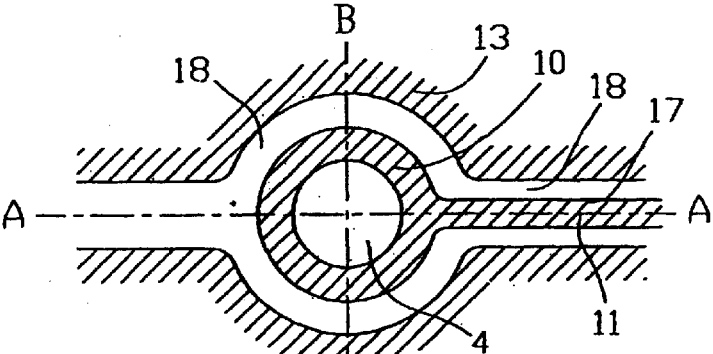

As shown in FIG. 2b, an insulating chamber 18 is etched into the substrate, preferably through the thickness of conducting layer 11, so as to insulate the transducer element from other portions of the substrate which may include other electrical components such as other transducer elements etched into the substrate. In one preferred embodiment, the width of insulating chamber 18 is about 100 μm. The insulating chamber 18 is etched into the substrate so as to form a wall 10 of a predetermined thickness, enclosing the cavity 4. A conducting line 17 is integrally made with wall 10 for connecting the transducer element to another electronic component, which is preferably etched into the same substrate, or to an external electronic circuit.

Figure 1A:
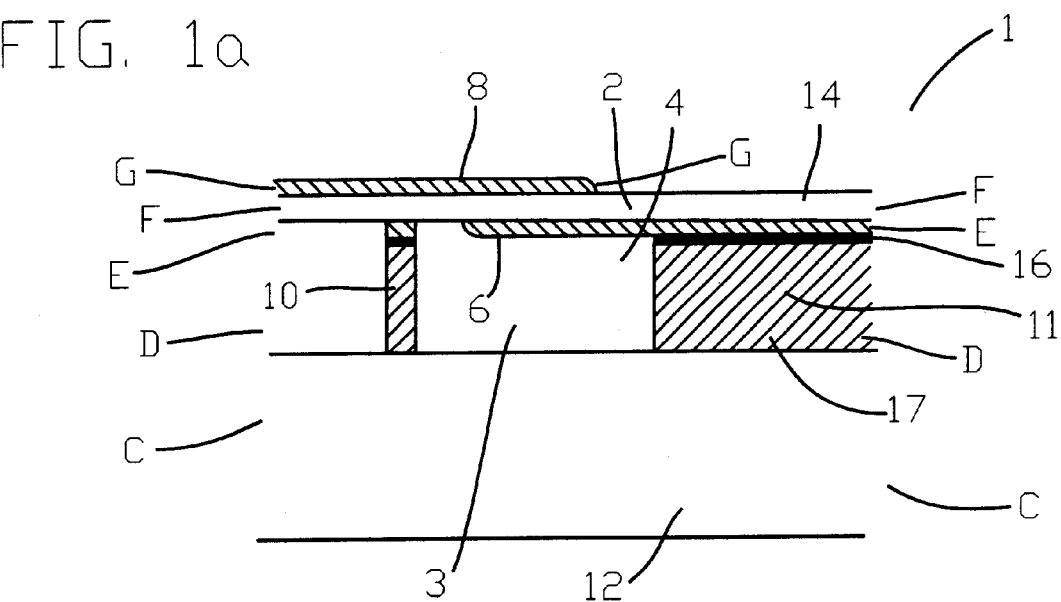
FIG. 1a is a longitudinal section of a preferred transducer element for use in an acoustic powered telemetric biosensor constructed in accordance with the present invention, taken along lines A—A in FIGS. 2a–2e.
Figure 1B:
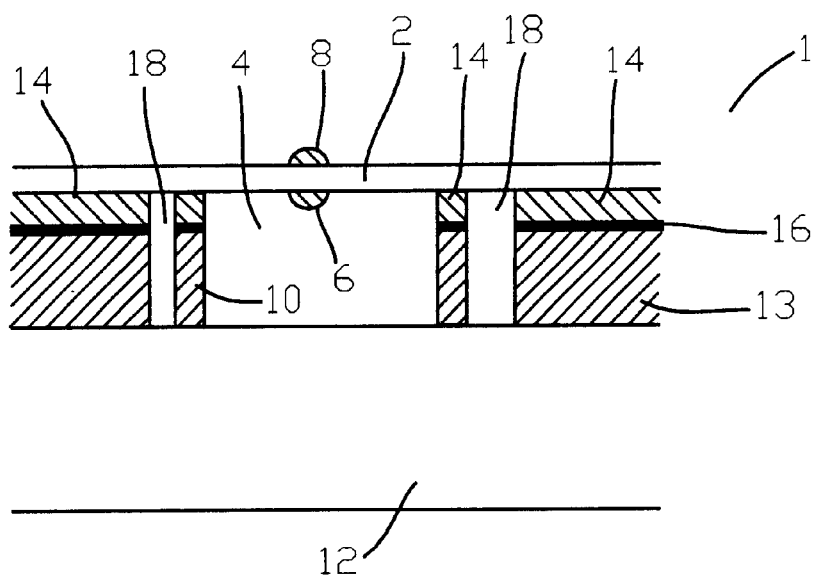
FIG. 1b is a longitudinal section of the transducer element of FIG. 1a, taken along lines B—B in FIGS. 2a–2e.
Figure 2C:
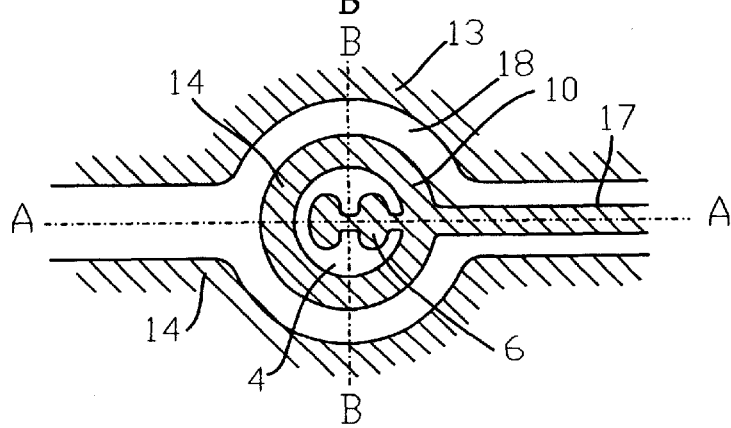
Figure 2D:
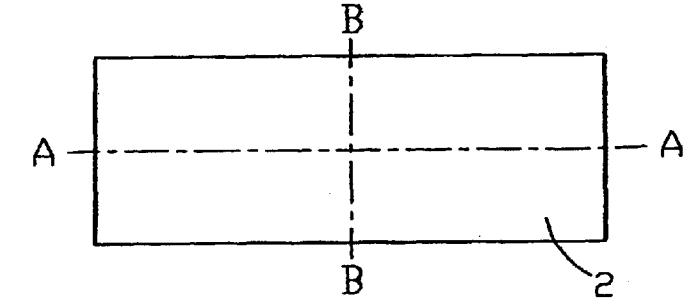
Figure 2E:
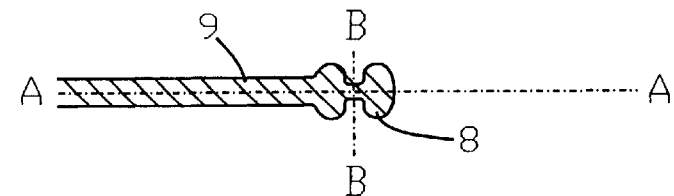

As shown in FIGS. 1a and 1b, attached to piezoelectric layer 2 are upper electrode 8 and lower electrode 6. As shown in FIGS. 2c and 2e, upper electrode 8 and lower electrode 6 are preferably precisely shaped so as to cover a predetermined area of piezoelectric layer 2. Electrodes 6 and 8 may be deposited on the upper and lower surfaces of piezoelectric membrane 2, respectively, by using various methods such as vacuum deposition, mask etching, painting, and the like.

As best seen in FIG. 1a, the lower electrode 6 is preferably made as an integral part of a substantially thin electrically conducting layer 14 disposed on electrically conducting layer 11. Preferably, electrically conducting layer 14 is made of a Nickel-Copper alloy and is attached to electrically conducting layer 11 by means of a sealing connection 16, which may be made of indium. In one preferred embodiment, the sealing connection 16 has a thickness of about 10 μm, such that the overall height of wall 10 of the cavity 4 is about 20–25 μm.

As shown in FIG. 2c, electrically conducting layer 14 covers the various portions of conducting layer 11, including wall 10 and conducting line 17. The portion of conducting layer 14 covering conducting line 17 is for connection to an electronic component such as a neighboring cell. In preferred embodiments, electrodes 6 and 8 are specifically shaped to include the most energy-productive region of piezoelectric layer 2. This configuration provides maximal response of the transducer while optimizing the electrode area, and therefore the cell capacitance, thereby maximizing a selected parameter such as voltage sensitivity, current sensitivity, or power sensitivity of the transducer element.

The vertical displacement of piezoelectric layer 2, Ψ, resulting from a monochromatic excitation at angular frequency ω is modeled using the standard equation for thin plates:

$$(\nabla^2 - \gamma^2)(\nabla^2 + \gamma^2)\Psi - \frac{3(1-\nu^2)}{2Qh^3}P + \frac{3iZ\omega(1-\nu^2)}{2Qh^3}\Psi = 0$$

wherein Q is the Young's modulus representing the elasticity of layer 2; h the half-thickness of layer 2; ν is the Poisson ratio for layer 2; γ is the effective wave number in the layer given by: $\gamma^4 = 3\rho(1-\nu^2)\omega^2/Qh^2$, wherein ρ is the density of layer 2 and ω is the angular frequency of the applied pressure (wherein the applied pressure may include the acoustic pressure, the static pressure differential across layer 2 and any other pressure the transducer comes across); Z is the mechanical impedance resulting from the coupling of layer 2 to both external and internal media of cavity 4, wherein the internal medium is preferably air and the external medium is preferably fluid; P is the acoustic pressure applied to layer 2, and $\overline{\Psi}$ represents the average vertical displacement of layer 2.

When cavity 4 is circular, the solution (given for a single frequency component ω) representing the dynamic displacement of a circular layer 2 having a predetermined radius a, expressed in polar coordinates, is:

$$\Psi(r, \varphi) = \frac{I_1(\gamma a)[J_0(\gamma r) - J_0(\gamma a)] + J_1(\gamma a)[I_0(\gamma r) - I_0(\gamma a)]}{2h\rho\omega^2 L_0(\gamma a) + i\omega Z L_2(\gamma a)} P$$

$$L_0(z) = I_0(z)J_1(z) + J_0(z)I_1(z), \ L_2(z) = J_2(z)I_1(z) - I_2(z)J_1(z)$$

$$Z = \frac{P_A}{i\omega H_A} + i\left[\frac{4}{3\pi} + \frac{1}{6}\right]\omega\rho_W a$$

wherein:
Ψ(r,φ) is time-dependent and represents the displacement of a selected point located on circular layer 2, the specific location of which is given by radius r and angle φ;

J and I are the normal and modified Bessel functions of the first kind, respectively;

$P_A$, $H_A$ are the air pressure within cavity 4 and the height of cavity 4, respectively; and $\rho_W$ is the density of body fluid external to the cavity 4 (e.g., in the aneurysmal sac 180 in FIG. 10), once the biosensor 172 is implanted.

The first term of the impedance Z relates to the stiffness resulting from compression of air within cavity 4, and the second term of Z relates to the mass added by the fluid boundary layer. An additional term of the impedance Z relating to the radiated acoustic energy is substantially negligible in this example.

The charge collected between electrodes 6 and 8 per unit area is obtained by evaluating the strains in layer 2 resulting from the displacements, and multiplying by the pertinent off-diagonal elements of the piezoelectric strain coefficient tensor, $e_{31}$, $e_{32}$, as follows:

$$Q(r, \varphi, t) = e_{31}\left(\frac{\partial \Psi}{\partial x}\right)^2 + e_{32}\left(\frac{\partial \Psi}{\partial y}\right)^2$$

wherein:
Q(r,φ,t) represents the charge density at a selected point located on circular layer 2, the specific location of which is given by radius r and angle φ;

x is the stretch direction of piezoelectric layer 2; y is the transverse direction (the direction perpendicular to the stretch direction) of layer 2;

$e_{31}$, $e_{32}$ are off-diagonal elements of the piezoelectric strain coefficient tensor representing the charge accumulated at a selected point on layer 2 due to a given strain along the x and y directions, respectively, which coefficients being substantially dissimilar when using a PVDF layer.

$\Psi$ is the displacement of layer 2, taken as the sum of the displacement for a given acoustic pressure P at frequency f, and the static displacement resulting from the pressure differential between the interior and exterior of cavity 4, which displacements being extractable from the equations given above.

The total charge accumulated between electrodes 6 and 8 is obtained by integrating $Q(r,\phi,t)$ over the entire area S of the electrode:

$$Q = \int_S Q(r, \varphi, t) d\vec{x}$$

The capacitance C of piezoelectric layer 2 is given by:

$$C = \frac{\varepsilon}{2h} \int_S d\vec{x},$$

wherein $\varepsilon$ is the dielectric constant of piezoelectric layer 2; and $2h$ is the thickness of piezoelectric layer 2.

Accordingly, the voltage, current and power responses of piezoelectric layer 2 are evaluated as follows:

$$V = \frac{2h \int_S Q(r, \varphi, t) d\vec{x}}{\varepsilon \int_S d\vec{x}}, I = 2i\omega \int_S Q(r, \varphi, t) d\vec{x},$$

$$W = \frac{4ih \left[\int_S Q(r, \varphi, t) d\vec{x}\right]^2}{\varepsilon \int_S d\vec{x}}$$

The DC components of Q are usually removed prior to the evaluation, since the DC currents are usually filtered out. The values of Q given above represent peak values of the AC components of Q, and should be modified accordingly so as to obtain other required values such as RMS values.

According to the above, the electrical output of the transducer expressed in terms of voltage, current and power responses depend on the AC components of Q, and on the shape S of the electrodes. Further, as can be seen from the above equations, the voltage response of the transducer may be substantially maximized by minimizing the area of the electrode. The current response, however, may be substantially maximized by maximizing the area of the electrode.

Figure 3:
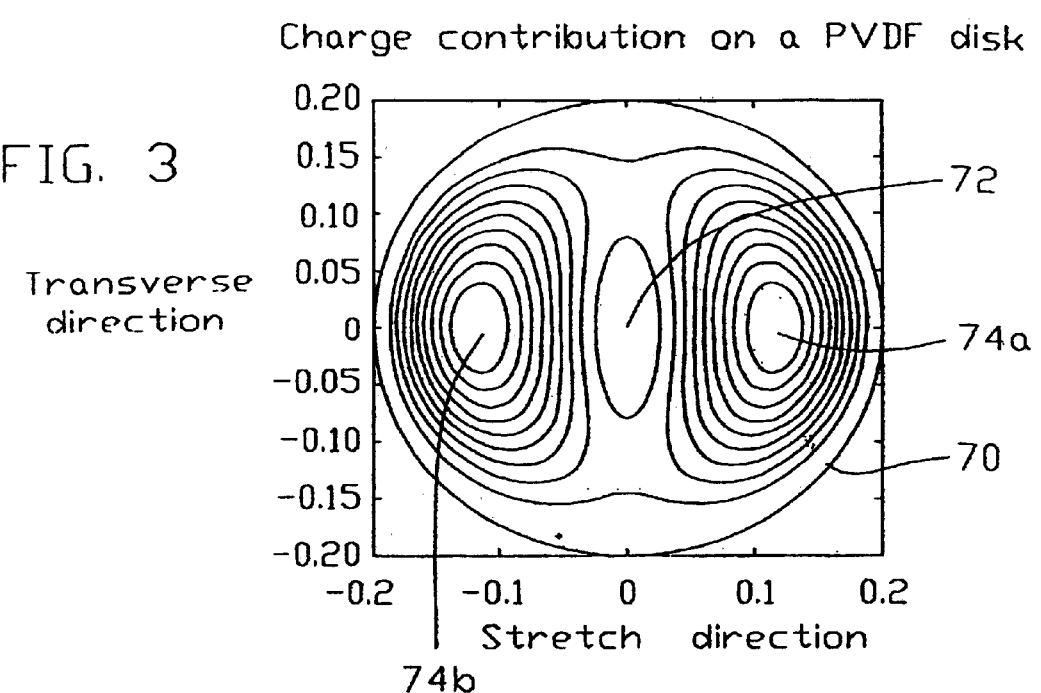
FIG. 3 shows the distribution of charge density across a piezoelectric layer of a preferred transducer element, resulting from the application of a constant pressure over the entire surface of the layer.
Figure 4A:
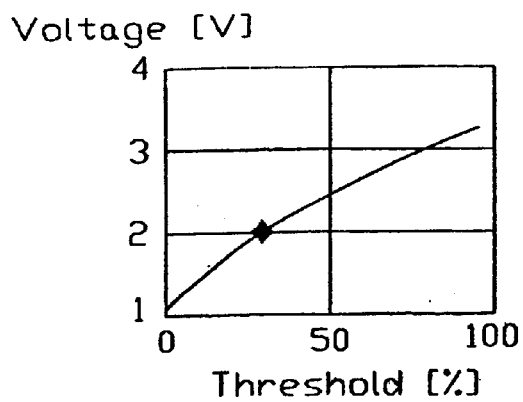
FIG. 4 shows the results of optimization performed for the power response of a preferred transducer element, constructed in accordance with the present invention.
Figure 4C:
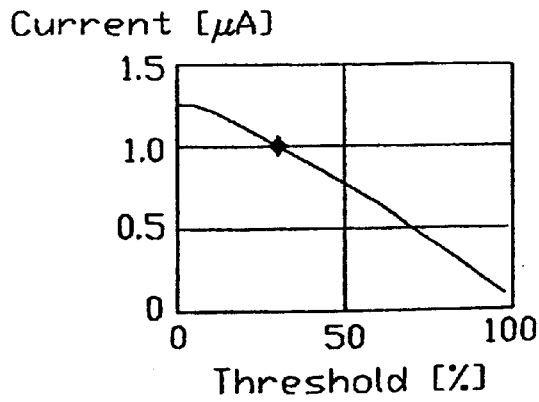
Figure 4B:
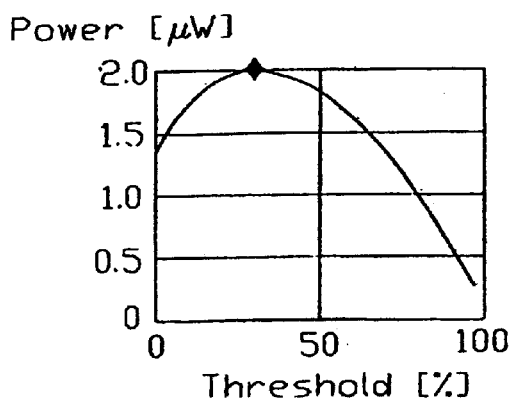
Figure 4D:
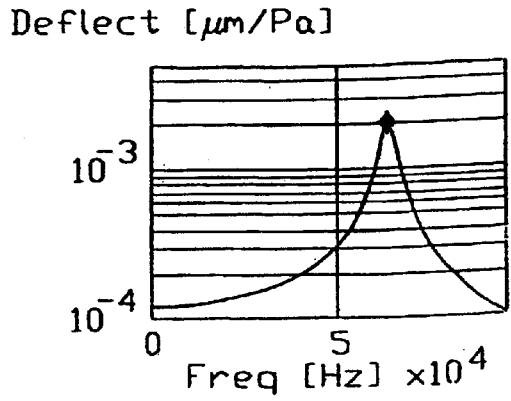

FIG. 3 shows the distribution of charge density on a circular piezoelectric layer 2 obtained as a result of pressure (acoustic and hydrostatic) applied uniformly over the entire area of layer 2, wherein specific locations on layer 2 are herein defined by using Cartesian coordinates including the stretch direction (x direction) and the transverse direction (y direction) of layer 2. It can be seen that distinct locations on layer 2 contribute differently to the charge density. The charge density vanishes at the external periphery 70 and at the center 72 of layer 2 due to minimal deformation of these portions. The charge density is maximal at two cores 74a and 74b located symmetrically on each side of center 72 due to maximal strains (in the stretch direction) of these portions.

A preferred strategy for optimizing the electrical responses of the transducer is to shape the electrode by selecting the areas contributing at least a selected threshold percentage of the maximal charge density, wherein the threshold value is the parameter to be optimized. A threshold value of 0% relates to an electrode covering the entire area of layer 2.

FIG. 4 shows the results of an optimization performed for the power response of a transducer having a layer 2 of a predetermined area. As shown in the figure, the threshold value which provides an optimal power response is about 30% (graph b). Accordingly, an electrode which covers only the portions of layer 2 contributing at least 30% of the maximal charge density yields a maximal power response. The pertinent voltage response obtained by such an electrode is higher by a factor of 2 relative to an electrode completely covering layer 2 (graph a). The current response obtained by such electrode is slightly lower relative to an electrode completely covering layer 2 (graph c). Further as shown in the figure, the deflection of layer 2 is maximal when applying an acoustic signal at the resonant frequency of layer 2 (graph d).

Figure 5:
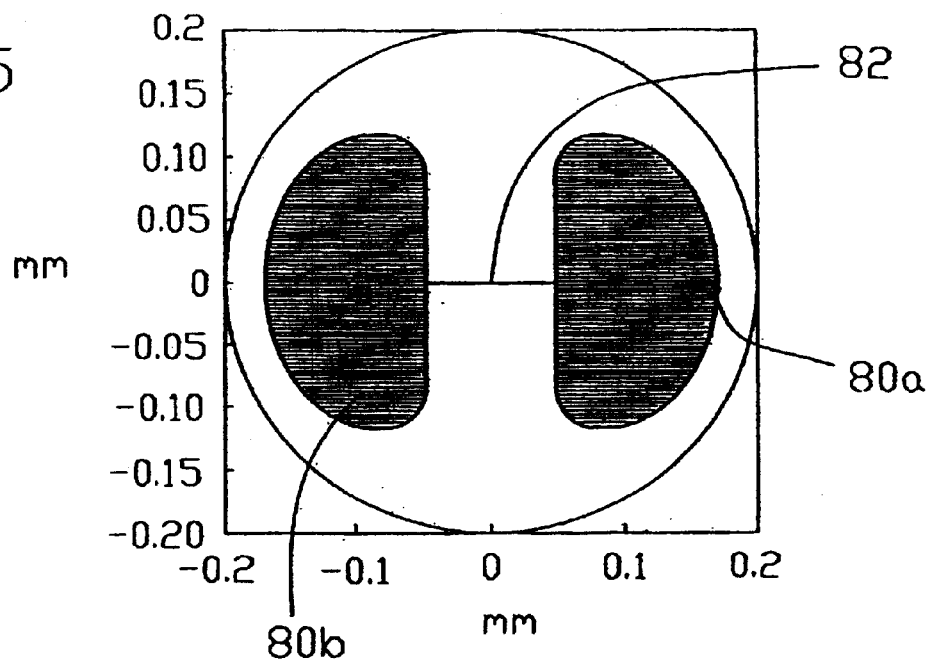
FIG. 5 shows a preferred electrode shape for maximizing the power response of a preferred transducer element, constructed in accordance with the present invention.

A preferred electrode shape for maximizing the power response of the transducer is shown in FIG. 5, wherein the electrode includes two electrode portions 80a and 80b substantially covering the maximal charge density portions of layer 2, the electrode portions being interconnected by means of a connecting member 82 having a minimal area. Preferably, portions 80a and 80b cover the portions of layer 2, which yield at least a selected threshold (e.g. 30%) of the maximal charge density.

In accordance with this aspect of the present invention, other parameters may be optimized so as to determine the shape of electrodes 6 and 8. For example, one electrode (upper electrode 8 or lower electrode 6) may be shaped so as to provide maximal electrical response of the transducer, with the other electrode covering the entire area of layer 2. Since the charge is collected only at the portions of layer 2 received between upper electrode 8 and lower electrode 6, such configuration is operatively equivalent to a configuration including two shaped electrodes having identical shapes.

Figure 6:
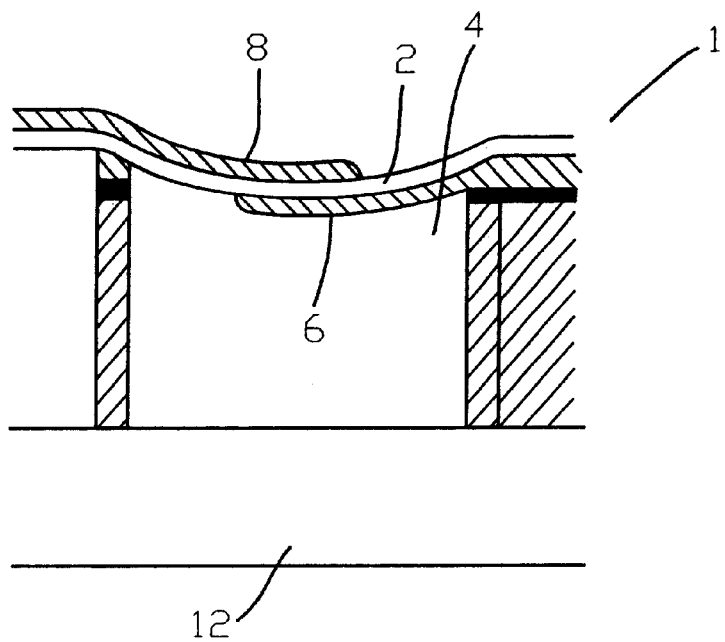
FIG. 6 is a longitudinal section of an alternate preferred transducer element for use in an acoustic powered telemetric deep-implant biosensor constructed in accordance with the present invention, which is configured to function as a transmitter.

Referring to FIG. 6, in one preferred embodiment, cavity 4 of transducer element 1 may contain gas of substantially low pressure, thereby conferring a substantially concave shape to piezoelectric membrane 2 at equilibrium. Such a configuration enables to further increase the electrical response of the transducer by increasing the total charge obtained for a given displacement of layer 2. The total displacement in such an embodiment is given by: $\Psi = P_0 \Psi_{DC} + P \Psi_{AC} \cos \omega t$, wherein $P_0$ is the static pressure differential between the exterior and the interior of cavity 4; $\Psi_{DC}$ is the displacement resulting from $P_0$; P is the amplitude of the acoustic pressure; and $\Psi_{DC}$ the displacement resulting from P.

Accordingly, the strain along the x direction includes three terms as follows:

$$S_{xx} = \left(\frac{\partial \Psi}{\partial x}\right)^2 = P_0^2 \left(\frac{\partial \Psi_{DC}}{\partial x}\right)^2 + P^2 \left(\frac{\partial \Psi_{AC}}{\partial x}\right)^2 \cos^2 \omega t + 2P_0 P \frac{\partial \Psi_{DC}}{\partial x} \frac{\partial \Psi_{AC}}{\partial x} \cos \omega t$$

wherein the DC component is usually filtered out.

Thus, by decreasing the pressure of the medium within the cavity (preferably air) relative to the pressure within the body at the implant site, (normally fluid), the value of $P_0$ is increased, thereby increasing the value of the third term of the above equation.

This preferred transducer construction makes it possible to increase the charge output of layer 2 for a given displacement, thereby increasing the voltage, current and power responses of the transducer without having to increase the acoustic pressure P. Also, this construction enables further miniaturization of the transducer element, same electrical response may obtain for smaller acoustic deflections. Such an embodiment is substantially more robust mechanically and therefore more durable than the embodiment shown in FIGS. 1a and 1b. Such further miniaturization of the transducer enables to use higher resonance frequencies relative to the embodiment shown in FIGS. 1a and 1b.

Preferably, a transducer element 1 according to the present invention is fabricated by using technologies, which are in wide use in the microelectronics industry so as to allow integration thereof with other conventional electronic components. When the transducer element includes a substrate such as Copper-polymer laminate or silicon, a variety of conventional electronic components may be fabricated onto the same substrate.

According to one aspect of the present invention, a plurality of cavities 4 may be etched into a single substrate 12 and covered by a single piezoelectric layer 2 so as to provide a transducer element including a matrix of transducing cells members 3. Such an arrangement provides a larger energy collecting area of predetermined dimensions, while still retaining the advantage of miniature individual transducing cell members 3. With this configuration, the transducing cell members 3 may be electrically interconnected in parallel or serial connections, or combinations thereof, so as to tailor the voltage and current response of the transducer. Parallel connections are preferably used so as to increase the current output while serial connections are preferably used so as to increase the voltage output of the transducer. Further, piezoelectric layer 2 may be completely depolarized and then re-polarized at specific regions thereof so as to provide a predetermined polarity to each of the transducing cell members 3. This configuration enables to reduce the complexity of interconnections between the cell members 3.

A preferred biosensor transducer element according to the present invention may be further used as a transmitter element for transmitting information to a remote (e.g., external to the body) receiver by modulating the reflection of an external impinging acoustic wave arrived from a remote transmitter.

Towards this end, referring to FIG. 6, the transducer element shown may function as a transmitter element due to the asymmetric fluctuations of piezoelectric layer 2 with respect to positive and negative transient acoustic pressures obtained as a result of the pressure differential between the interior and exterior of cavity 4.

A transmitter element according to the present invention preferably modulates the reflection of an external impinging acoustic wave by means of a switching element connected thereto. The switching element encodes the information that is to be transmitted, such as the output of a sensor, thereby frequency modulating a reflected acoustic wave. Such configuration requires very little expenditure of energy from the transmitting module itself, since the acoustic wave that is received is externally generated, such that the only energy required for transmission is the energy of modulation.

Specifically, the reflected acoustic signal is modulated by switching the switching element according to the frequency of a message electric signal arriving from another electronic component such as a sensor, so as to controllably change the mechanical impedance of layer 2 according to the frequency of the message signal. Preferably, a specific array of electrodes connected to a single cell member 3, or to a plurality of cell members, are used to control the mechanical impedance of layer 2.

Figure 7A:
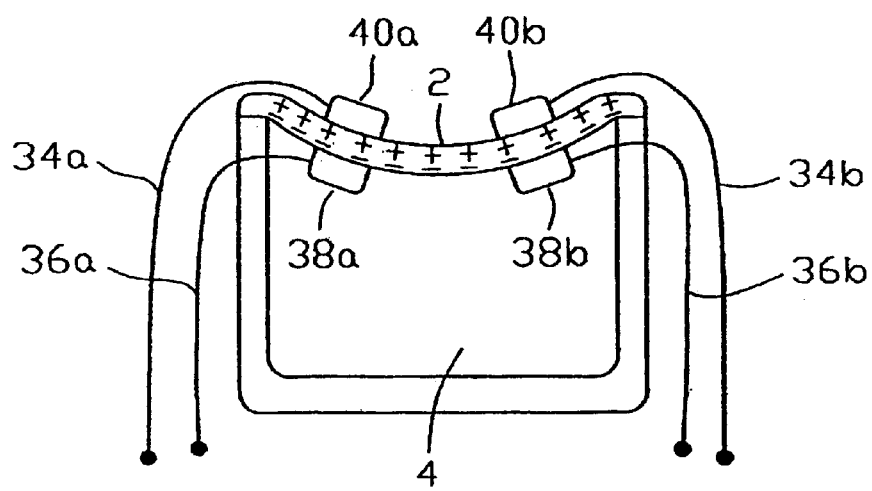
Figure 7B:
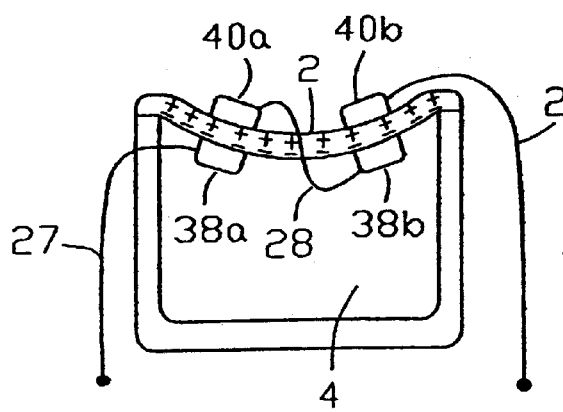

FIGS. 7a–7g illustrate possible configurations for controllably change the impedance of layer 2 of a transmitter element. Referring to FIG. 7a, a transmitter element according to the present invention may include a first and second pairs of electrodes, the first pair including an upper electrode 40a and a lower electrode 38a, and the second pair including an upper electrode 40b and a lower electrode 38b. Electrodes 38a, 38b, 40a and 40b are electrically connected to an electrical circuit by means of conducting lines 36a, 36b, 34a and 34b, respectively, the electrical circuit including a switching element (not shown) so as to alternately change the electrical connections of conducting lines 36a, 36b, 34a and 34b.

Preferably, the switching element switches between a parallel connection and an anti-parallel connection of the electrodes. A parallel connection decreases the mechanical impedance of layer 2, wherein an anti-parallel connection increases the mechanical impedance of layer 2. An anti-parallel connection may be obtained by interconnecting line 34a to 36b and line 34b to 36a. A parallel connection may be obtained by connecting line 34a to 34b and line 36a to 36b. Preferably, the switching frequency equals the frequency of a message signal arriving from an electrical component such as a sensor.

According to another embodiment (FIG. 7b), upper electrode 40a is connected to lower electrode 38b by means of a conducting line 28, and electrodes 38a and 40b are connected to an electrical circuit by means of conducting lines 27 and 29, respectively, the electrical circuit including a switching element. Such configuration provides an anti-parallel connection of the electrodes, wherein the switching element functions as an on/off switch, thereby alternately increasing the mechanical impedance of layer 2.

Figure 7C:
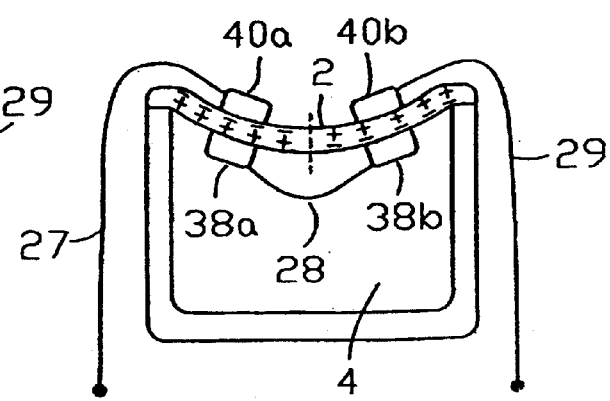

In order to reduce the complexity of the electrical connections, layer 2 may be depolarized and then re-polarized at specific regions thereof. As shown in FIG. 7c, the polarity of the portion of layer 2 received between electrodes 40a and 38a is opposite to the polarity of the portion of layer 2 received between electrodes 40b and 38b. An anti-parallel connection is thus achieved by interconnecting electrodes 38a and 38b by means of a conducting line 28, and providing conducting lines 27 and 29 connected to electrodes 40a and 40b, respectively, the conducting lines for connection to an electrical circuit including a switching element.

In another embodiment, the transmitting element includes a plurality of transducing cell members, such that the mechanical impedance of layer 2 controllably changed by appropriately interconnecting the cell members.

As shown in FIG. 7d, a first transducing cell member 3a including a layer 2a and a cavity 4a, and a second transducing cell member 3b including a layer 2b and a cavity 4b are preferably contained within the same substrate; and layers 2a and 2b are preferably integrally made (not shown). A first pair of electrodes including electrodes 6a and 8a is attached to layer 2, and a second pair of electrode including electrodes 6b and 8b is attached to layer 2b. Electrodes 6a, 8a, 6b and 8b are electrically connected to an electrical circuit by means of conducting lines 37a, 35a, 37b and 35b, respectively, the electrical circuit including a switching element so as to at alternately switch the electrical connections of conducting lines 37a, 35a, 37b and 35b so as to alternately provide parallel and anti-parallel connections, substantially as described for FIG. 7a, thereby alternately decreasing and increasing the mechanical impedance of layers 2a and 2b.

FIG. 7e illustrates yet another embodiment, wherein the first and second transducing cell members are interconnected by means of an anti-parallel connection. The polarity of layer 2a is opposite to the polarity of layer 2b so as to reduce the complexity of the electrical connections between cell members 3a and 3b. Thus, electrode 6a is connected to electrode 6b by means of a conducting line 21, and electrodes 8a and 8b are provided with conducting lines 20 and 22, respectively, for connection to an electrical circuit including a switching element, wherein the switching element preferably functions as an on/off switch so as to alternately increase the mechanical impedance of layers 2a and 2b.

FIG. 7f shows still another embodiment, wherein the first and second transducing cell members are interconnected by means of a parallel connection. Electrodes 6a and 6b are interconnected by means of conducting line 24, electrodes 8a and 8b are interconnected by means of conducting line 23, and electrodes 6b and 8b are provided with conducting lines 26 and 25, respectively. The respective conducting lines for connection to an electrical circuit include a switching element, which preferably functions as an on/off switch for alternately decreasing and increasing the mechanical impedance of layers 2a and 2b.

Figure 8:
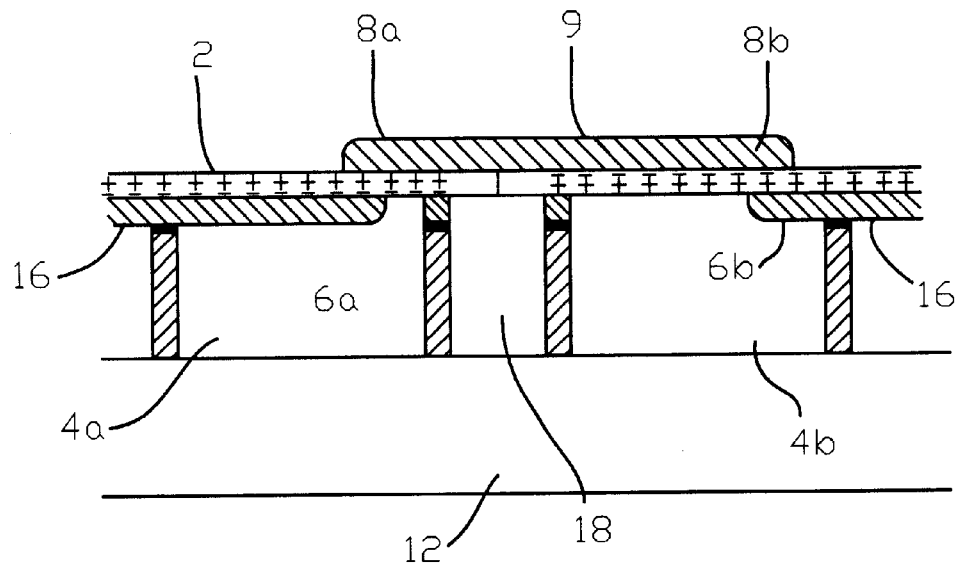
FIG. 8 is a longitudinal section of a preferred acoustic transmitter element constructed in accordance with the present invention, including an anti-parallel electrical connection.

FIG. 8 shows a possible configuration of two transducing cell members etched onto the same substrate and interconnected by means of an anti-parallel connection. The transducing cell members are covered by a common piezoelectric layer 2, wherein the polarity of the portion of layer 2 received between electrodes 6a and 8a is opposite to the polarity of the portion of layer 2 received between electrodes 6b and 8b. Electrodes 8a and 8b are bonded by means of a conducting line 9 and electrodes 6a and 6b are provided with conducting lines 16 for connection to an electrical circuit.

Figure 9:
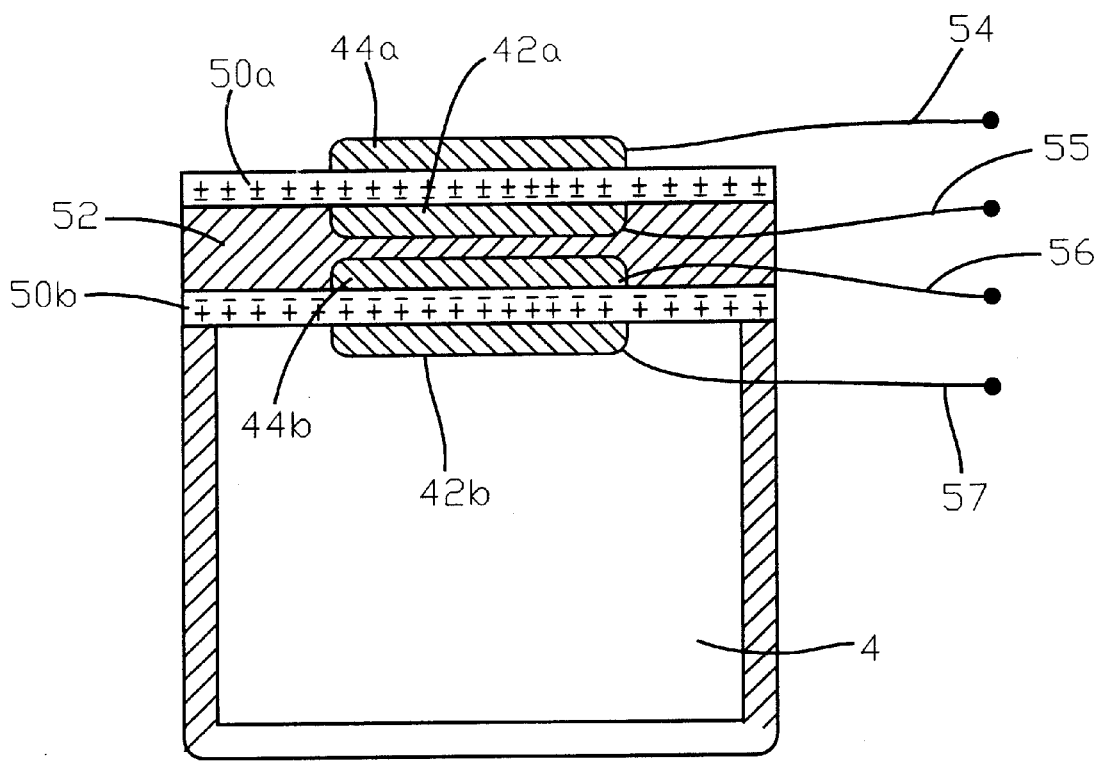
FIG. 9 is a longitudinal section of another embodiment of an acoustic transmitter element constructed in accordance with the present invention.

Another preferred embodiment of an acoustic biosensor transmitter element is shown in FIG. 9, and includes a transducing cell member having a cavity 4 covered by a first and second piezoelectric layers, 50a and 50b, preferably having opposite polarities. Preferably, layers 50a and 50b are interconnected by means of an insulating layer 52. Attached to layer 50a are upper and lower electrodes 44a and 42a, and attached to layer 50b are upper and lower electrodes 44b and 42b. Electrodes 44a, 42a, 44b and 42b are provided with conducting lines 54, 55, 56 and 57, respectively, for connection to an electrical circuit.

While preferred transducer constructions and embodiments for use in an implantable acoustic biosensor in accordance with the present invention have been shown and described, as would be apparent to those skilled in the art, many modifications and applications are possible without departing from the inventive concepts herein.

For example, although the preferred acoustic biosensor embodiments described herein employ a transducer element to both convert acoustic energy to electrical power and to transmit the physiological information signal, it may be desirable for certain biosensor devices, and in certain implant locations, e.g., due to power needs and/or tissue depth, to employ the transducer only as an transmitter/receiver and not as an energy converter. Instead, a battery, such as a lithium battery used in implantable pacemakers, may be employed in an implantable acoustic biosensor contemplated by the invention.

Thus, the scope of the disclosed invention is not to be restricted except in accordance with the appended claims.

What is claimed is:

1. An acoustic biosensor for implantation in a body, comprising:
    a sensor element for measuring a physiological condition and for generating a signal representative of the physiological condition, and
    a transducer element for energizing the sensor element, the transducer comprising
        a cell member having a cavity,
        a piezoelectric layer attached to the cell member, the piezoelectric layer having an external surface and an internal surface, the piezoelectric layer configured so as to enable fluctuations thereof at its resonance frequency upon impinging of an external acoustic wave,
        a first electrode attached to the external surface, and
        a second electrode attached to the internal surface, the first and second electrodes configured to generate electrical current from vibrations of the transducer element caused by an acoustic signal.

2. The biosensor of claim 1, wherein the cavity is etched into a substrate.

3. The biosensor of claim 2, wherein the substrate includes a plurality of cell members.

4. The biosensor of claim 1, wherein at least one of the first and second electrodes is specifically shaped so as to provide a maximal electrical output.

5. An acoustic biosensor for implantation in a body, comprising:
    a sensor element for measuring a physiological condition and for generating a sensor signal representative of the physiological condition; and
    a transducer element coupled to the sensor element for transmitting a signal out of the body, the transducer element comprising
        a cell member having a cavity,
        a flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave,
        a first electrode attached to the external surface, and
        a second electrode attached to the internal surface, the first and second electrodes being electrically connected to an electrical circuit including a switching element for controllably changing the mechanical impedance of the piezoelectric layer in accordance with an electrical message signal.

6. An acoustic biosensor for monitoring a physiological condition at an implantation site in a body, comprising:
    a sensing element for measuring the physiological condition at the implantation site and for generating an information signal representative of the physiological condition; and
    a transducer element for converting an acoustic interrogation signal into energy for operating the sensor and for modulating the interrogation signal to transmit the information signal.

7. An acoustic biosensor for implantation in a body, comprising:
    a sensor element for measuring a physiological condition and for generating a signal representative of the physiological condition, and
    a transducer element configured to energize the sensor element, the transducer comprising
        a cell member having a cavity, a piezoelectric layer attached to the cell member, the piezoelectric layer having an external surface and an internal surface, the piezoelectric layer configured so as to enable fluctuations thereof at its resonance frequency upon impinging of an acoustic wave received from a source located outside the body, a first electrode attached to the external surface, and a second electrode attached to the internal surface, the first and second electrodes configured to generate electrical current from vibrations of the transducer element caused by the acoustic wave.

8. The biosensor of claim 7, wherein the cavity is etched into a substrate.

9. The biosensor of claim 8, wherein the substrate includes a plurality of cell members.

10. The biosensor of claim 7, wherein at least one of the first and second electrodes is specifically shaped so as to provide a maximal electrical output.

11. The biosensor of claim 7, wherein the acoustic wave is generated by a transceiver outside the body.

* * * * *